(12) United States Patent
DiCaprio et al.

(10) Patent No.: US 6,565,595 B1
(45) Date of Patent: May 20, 2003

(54) TWO COMPONENT SLEEVES

(75) Inventors: Fernando DiCaprio, Mendota Heights, MN (US); Joseph M. Lyver, Hopkins, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/664,267

(22) Filed: Sep. 18, 2000

(51) Int. Cl.⁷ .................................................. A61F 2/06
(52) U.S. Cl. ...................................................... 623/1.11
(58) Field of Search .......................... 606/1, 108, 194, 606/195, 198; 623/1.1, 1.11, 12, 1.12

(56) References Cited

U.S. PATENT DOCUMENTS

| | | | |
|---|---|---|---|
| 4,950,227 A | 8/1990 | Savin et al. | 604/8 |
| 5,108,416 A | 4/1992 | Ryan et al. | 606/194 |
| 5,403,341 A | 4/1995 | Solar | 606/198 |
| 5,445,646 A * | 8/1995 | Euteneuer et al. | |
| 5,662,703 A | 9/1997 | Yurek et al. | 623/1 |
| 5,800,517 A * | 9/1998 | Anderson et al. | 623/1 |
| 5,968,069 A | 10/1999 | Dusbabek et al. | 606/194 |
| 5,980,530 A | 11/1999 | Willard et al. | 606/108 |
| 6,059,813 A | 5/2000 | Vrba et al. | 606/198 |
| 6,068,634 A * | 5/2000 | Cornelius et al. | 606/108 |
| 6,132,458 A * | 10/2000 | Staehle et al. | 623/1.11 |
| 6,174,316 B1 | 1/2001 | Tuckey et al. | 606/108 |
| 6,183,505 B1 | 2/2001 | Mohn, Jr. et al. | 623/1.11 |
| 6,221,097 B1 * | 4/2001 | Wang et al. | |

FOREIGN PATENT DOCUMENTS

EP  0 897 730  2/1999

OTHER PUBLICATIONS

U.S. patent application Ser. No. 09/664,268, ScottHanson, filed on Sep. 18, 2000.
U.S. patent application Ser. No. 09/427,805, L. Wang, filed on Oct. 27, 1999.

* cited by examiner

Primary Examiner—Michael H. Thaler
(74) Attorney, Agent, or Firm—Vidas, Arrett & Steinkraus, P.A.

(57) ABSTRACT

A stent retaining sleeve which may be employed with a stent delivery system. The sleeves having two tubular components which are engaged to one another. The first component is an elastomeric tube which is designed to be disposed about the end of a stent and the portion of the catheter immediately adjacent thereto. The first component includes an inner surface which may be at least partially prelubricated with a lubricant. The second sleeve component is a second elastomeric tube which partially overlaps at least a portion of the first tube and is engaged thereto. A second portion of the second tube is constructed and arranged to engage a portion of the catheter shaft immediately adjacent thereto.

29 Claims, 5 Drawing Sheets

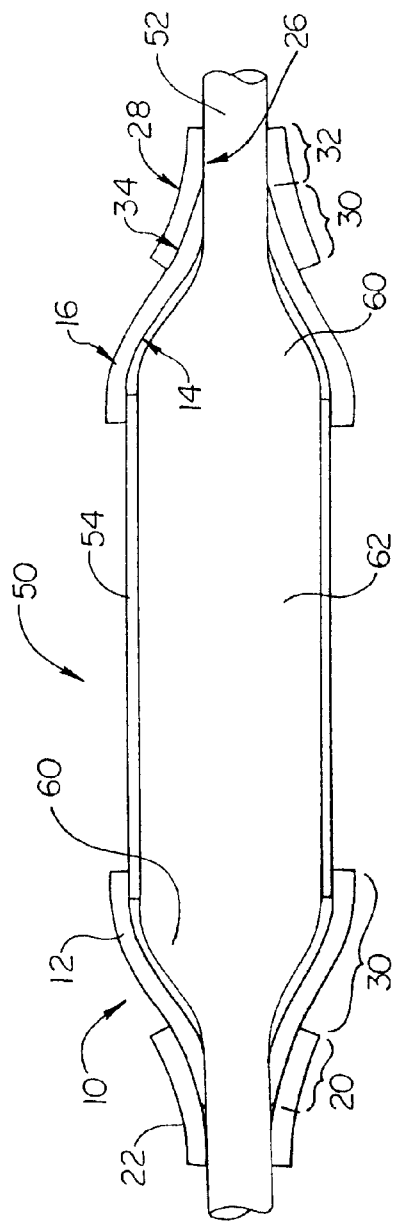
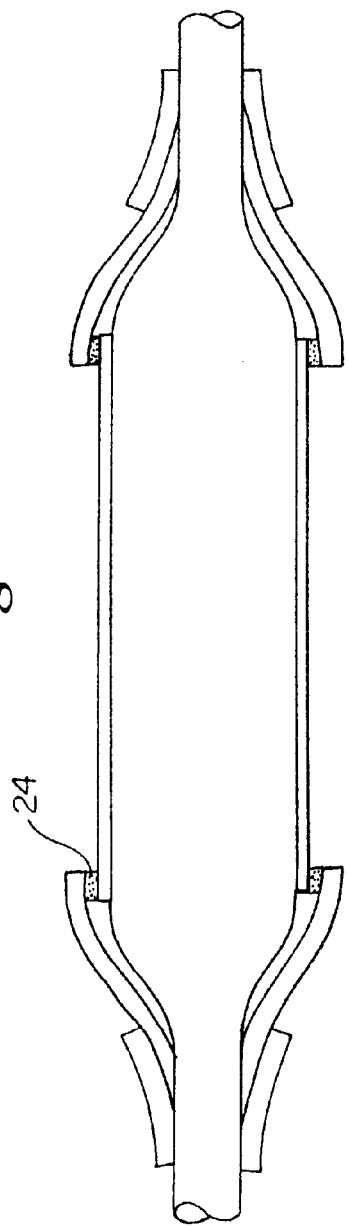

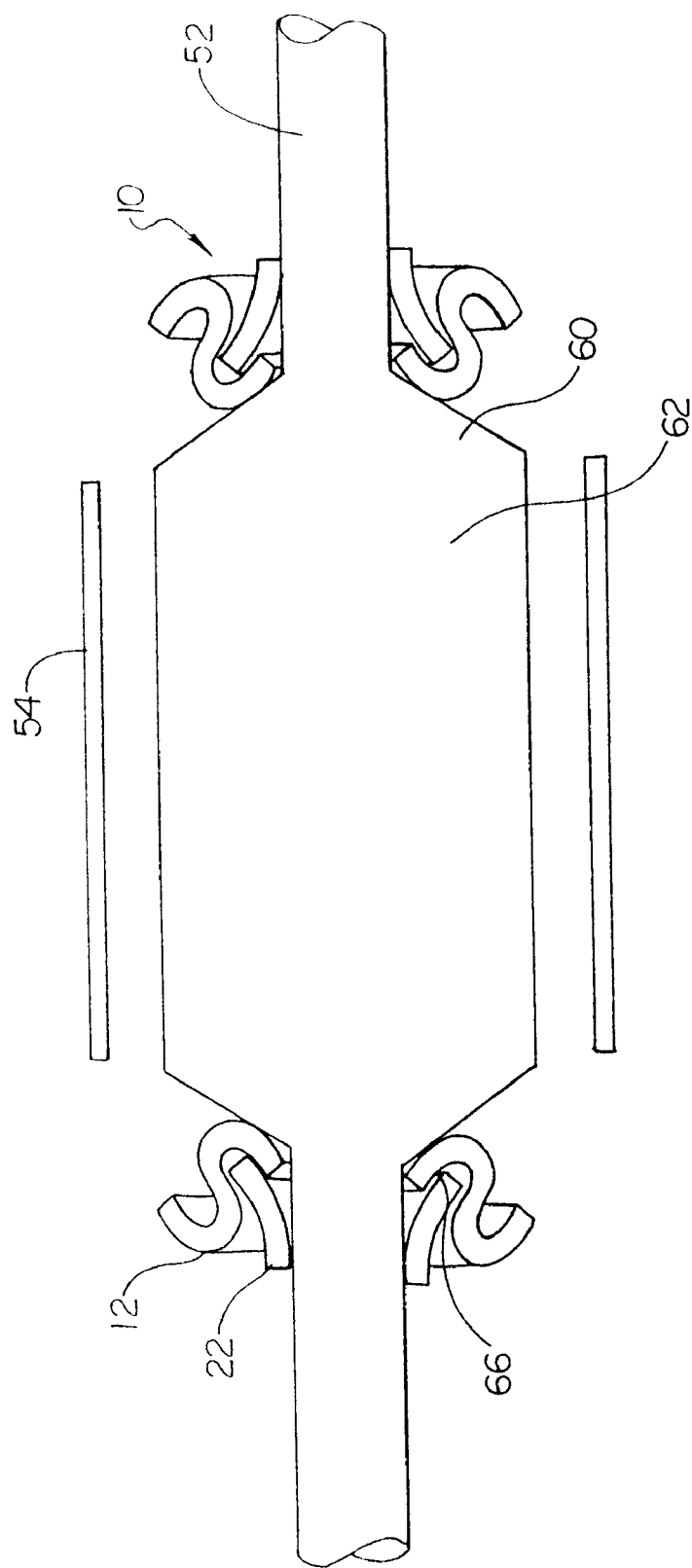

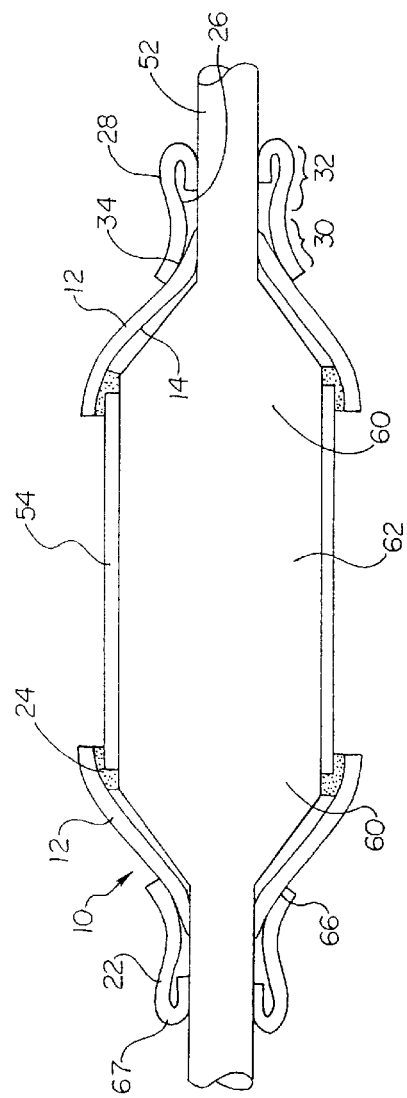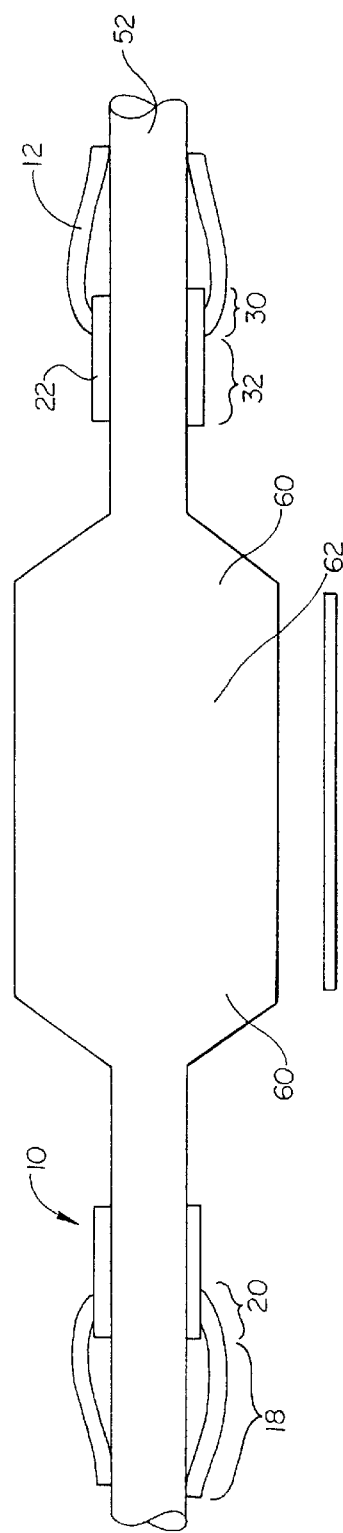

TWO COMPONENT SLEEVES

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to a medical device delivery systems. More particularly the present invention is directed to stent delivery systems which employ stent retaining socks or sleeves which aid in retaining the stent to the catheter prior to delivery of the stent into a body vessel. The present invention provides for stent end retaining sleeves, wherein each sleeve has two components which are engaged to one another. In at least one embodiment of the invention the sleeve or sleeves are composed of a first tubular portion of material such as polyurethane, the material may be lubricious or have alubricious coating thereupon. The sleeve may also have a second tubular portion composed of a polyurethane-polycarbonate blend such as a mixture of Carbothane™ and Chronoflex™. The second tube has a first end which at least partially overlaps and is engaged to a portion of the first tube. In at least one embodiment of the invention first end of the second tube and at least a portion of the first tube are connected together. A second portion of the second tube is designed to engage a portion of a catheter shaft, while a portion of the first tube is constructed and arranged to be disposed about a stent prior to stent delivery. Other inventive aspects and embodiments of the present end retaining sleeves will be made apparent below.

2. Description of the Related Art

Stents and stent delivery assemblies are utilized in a number of medical procedures and situations and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents may be crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s) of the stent toehold it in place on the catheter in a contracted condition. Each sleeve is elastomeric in nature so as to stretch and release the stent when it expands for implantation. The stent is expandable by means of the expandable balloon on the catheter. During expansion of the stent at the deployment site, the stent margins are freed of the protective sleeve(s). As indicated above, the present invention is particularly directed to stent retaining sleeves having at least two components. In addition to the above, other types of stent delivery sleeves are known.

In some stent delivery devices, a lubricant is applied to the inside surface of the sleeve or the sleeve itself is made to be particularly lubricious. A problem with providing such lubricity is that the lubrication tends to be applied to the entire sleeve, including the portion of the sleeve which is to be affixed to the catheter shaft. The presence of lubrication on the portion of the sleeve which is to be affixed may make it difficult to engage the sleeve to the catheter. In some alternative sleeve arrangements one or more lubricants are added after the sleeve is mounted onto the catheter, but such after-the-fact lubrication is often difficult to apply and may result in uneven lubrication of the sleeve.

The present invention addresses these and other problems associated with many prior sleeve designs by providing each sleeve with two portions, a first portion which is intended to overlie the ends of a stent and which may have an internal surface, which in-whole or in-part, is inherently lubricious or has a lubricant applied thereto, and a second portion which at least partially overlies the first portion and which has an internal surface which may be readily engaged to the catheter shaft as well as the outer surface of the first portion of the sleeve. The overlap between the first portion and second portion also provides the sleeve with a buckle or break point which enhances the capacity of the first portion of the sleeve to retract off of the sleeve as described in detail below. The two portions may be connected to one another by an interference fit, bonding, or welding, such as laser welding.

The entire content of all patents and applications listed within the present patent application are incorporated herein by reference.

BRIEF SUMMARY OF THE INVENTION

This invention provides for a stent retaining sleeve or sleeves which may be employed with a stent delivery system. The inventive sleeves have two components which are engaged to one another. The first component is an elastomeric tube which is designed to be disposed about the end of a stent and the portion of the catheter immediately adjacent thereto. The first component is a tubular portion of sleeve material which includes an inner surface as well as an outer surface both of which may be at least partially lubricated. The second sleeve component is a second tube of sleeve material which is preferably constructed of a different material than the first tube material. In at least one embodiment of the invention the material of the second component has a greater durometer Shore D hardness than that of the first component. A first portion of the.second component overlaps at least a portion of the first component and is engaged thereto. A second portion of the second, component is constructed and arranged to engage a portion of the catheter shaft immediately adjacent thereto. In at least one embodiment of the invention the sleeve may be mounted singly or in pairs about the end or ends, respectively, of a stent on a stent delivery catheter. Where the sleeve or sleeves are utilized in a stent delivery system, the sleeve or sleeves are constructed and arranged to readily retract off of the end or ends of the stent when the stent exerts an outwardly acting radial force on the portion of the sleeve(s) overlying the stent.

BRIEF DESCRIPTION OF THE SEVERAL VIEWS OF THE DRAWINGS

A detailed description of the invention is hereafter described with specific reference being made to the drawings in which:

FIG. 3 is a side view of an embodiment of the invention;

FIG. 4 is a side view of an embodiment of the invention;

FIG. 7 is a side view of the embodiment shown in FIG. 3 in a potential post stent delivery state;

FIG. 8 is a side view of an embodiment of the invention; and

FIG. 9 is a side view of the embodiment of the invention shown in FIG. 8 in a potential post stent delivery state.

DETAILED DESCRIPTION OF THE INVENTION

Figure 1:
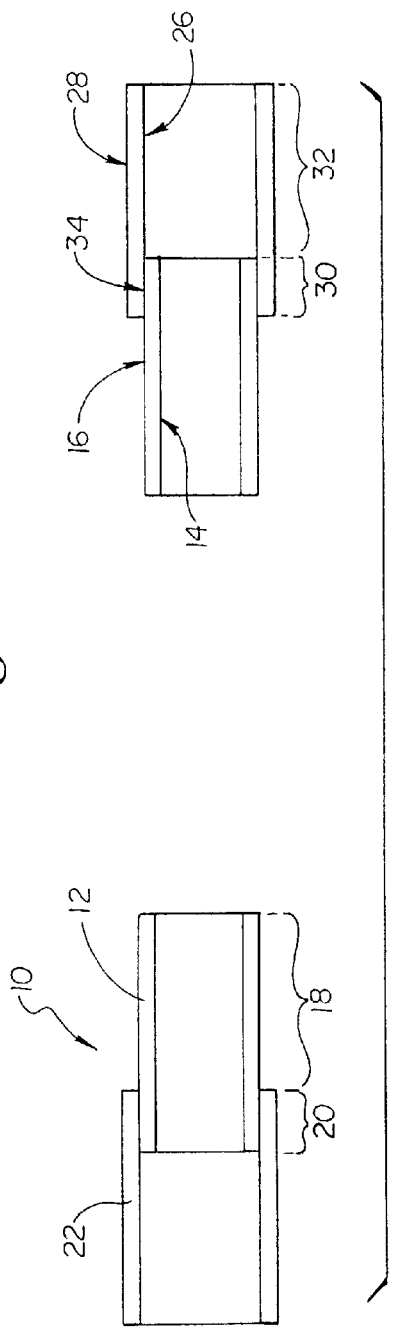
FIG. 1 is a side view of an embodiment of the invention.
Figure 2:
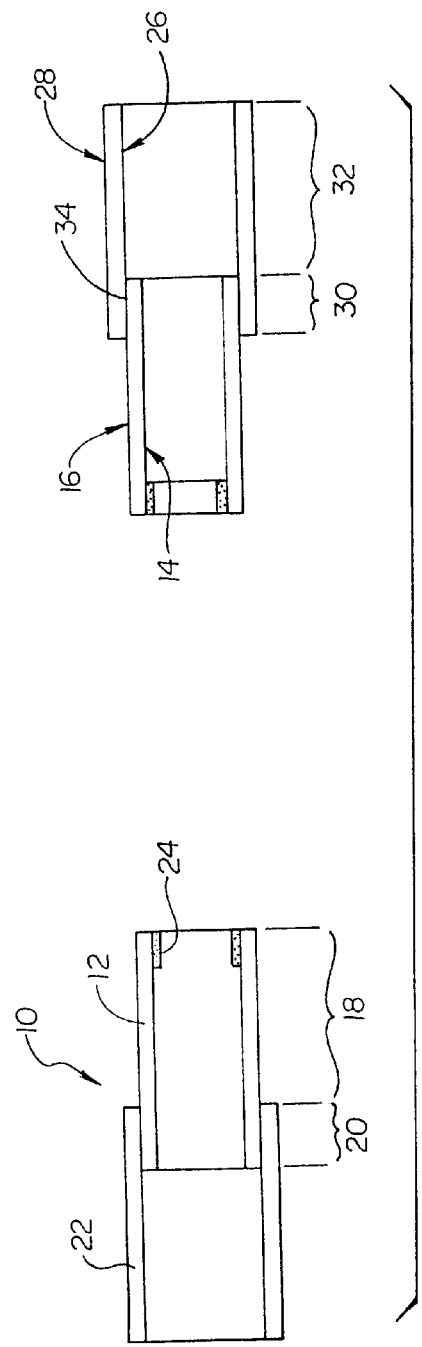
FIG. 2 is a side view of an embodiment of the invention.

In a basic embodiment, the present invention is directed to one or more stent retaining socks or sleeves such as the pair of sleeves, indicated generally at 10, shown in FIG. 1. The sleeves 10, may be employed on a stent delivery catheter, indicated generally at 50, such as is shown in FIGS. 3–9. Each of the various sleeves 10, are made up of a first tubular member 12 and a second tubular member 22. The first tubular member has an inside surface 14 and an outside surface 16, as well as a first section 18 and a second section 20.

In the embodiment shown in the various figures the first tubular member 12 may be made of one or more thermoplastic elastomers i.e. block copolymers; copolymers and terpolymers of ethylene; homopolymers, copolymers and terpolymers of propylene; ethylene a-olefins; polyesters; polyamides; polyurethanes, such as TECOTHANE™ a biocompatable medical grade aromic polyurethane available from Thermedics, Inc.; polycarbonates, vinyl copolymers; ionomer materials and so forth. More specifically, materials such as nylon, SELAR™, polyether-polyester block copolymers (i.e. HYTRBL™ from DuPont or ARNITEL™ from DSM, Netherlands), PEBAX™(polyether block amide copolymers), SURLYN™, polyethylene terephthalate, pblytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters or other similar extrudable thermoplastic, polymeric materials, and/or composites thereof may be utilized in the present invention.

The second tubular member 22, may be manufactured from a polyurethane, a polycarbonate-polyurethane co-polymer, one or more polyurethane-polycarbonate blends, or any combination thereof.

In the embodiment shown in FIGS. 1 the first tubular member 12 is made from TECOTHANE™, the second tubular member 22 is composed of a mixture of commercially available polycarbonate-polyurethane co-polymers CARBOTHANE™ from Thermedics, Inc. and CHRONOFLEX™ from CT Biomaterials. The precise combination of polycarbonate-polyurethane co-polymers in the second tubular member 22 may vary, but in the present embodiment the second tubular member 22 is composed of a 50/50 mixture of CARBOTHANE™ and CHRONOFLEX™. The second tubular member 22 may act to provide the sleeve 10 with a more rigid structure than the first tubular member 12 would alone.

The second tubular member 22 may also be provided with a greater hardness or durometer than the first tubular member 12. In the embodiments shown, the first tubular member 12 has a Shore D hardness no greater than 1055D as measured by the Shore D hardness scale; the second tubular member 22 has a Shore D hardness equal to or greater than that of the first tubular member 12. By providing the members 12 and 22 with various hardnesses, the sleeve 10 may be configured to provide a wide range of retraction characteristics.

The first tubular member 12 may be provide with a portion which is lubricious or may be coated with one or more lubricant or lubricants 24. The lubricant or lubricants may be hydrophobic and/or hydrophilic, and may be selected from, but are not limited to, one or more of the following substances: silicones; PVP (polyvinyl pyrrolidone); PPO (polypropylene oxide); PEO; BioSlide™ coating produced by SciMed (BioSlide™ is a hydrophilic lubricious coating comprising polyethylene oxide and neopentyl glycol diacrylate polymerized in a solution of water and isopropyl alcohol in the presence of a photoinitiator such as azobisisobutronitrile); oils, such as mineral oil, olive oil, vegetable oil, or other natural oils, and wax. Lubricant 24 may be applied to the inside surface 14 of the first tubular member 12 or any portion thereof Lubricant may also be applied to at least a portion of the first section 18 on the outside surface 16 as may be desired. Alternatively, in the embodiment shown in FIG. 1 the inside surface 14 may be plasma treated through exposure to a charged ion field to promote cross-linking, the resulting modified cross-linked surface having improved lubricious qualities which may alleviate any need for an extra lubricant such as previously described.

Additionally, the respective compositions of the first and second tubular members 12 and 22 are such that the materials may be bonded together. In the various embodiments shown in FIGS. 1–9 the outside surface 16 of the second portion 20 of the first tubular member 12 is engaged to the inside surface 26 of the first portion 30 of the second tubular member 22. The engagement may be by interference fit, chemical or physical bonding, or welding such as heat or laser welding, or any combination thereof. In the embodiment shown in FIG. 1 it may be seen that the portions 20 and 30 are laser welded together with a lap weld 34. The types or methods of engagement described above between portions 20 and 30 may also be utilized .to attach at least a part of the inside surface 26 of the second portion 32 of the second tubular member 28 to the shaft 52 of a balloon catheter 50 such as may be seen in FIGS. 3–5. Specifically, in FIG. 3 the inside surface 26 of section 32 is laser welded to the catheter shaft 52, however any of the previously mentioned engagement methods could be used to secure the sleeve 10 to the catheter shaft 52.

Figure 5:
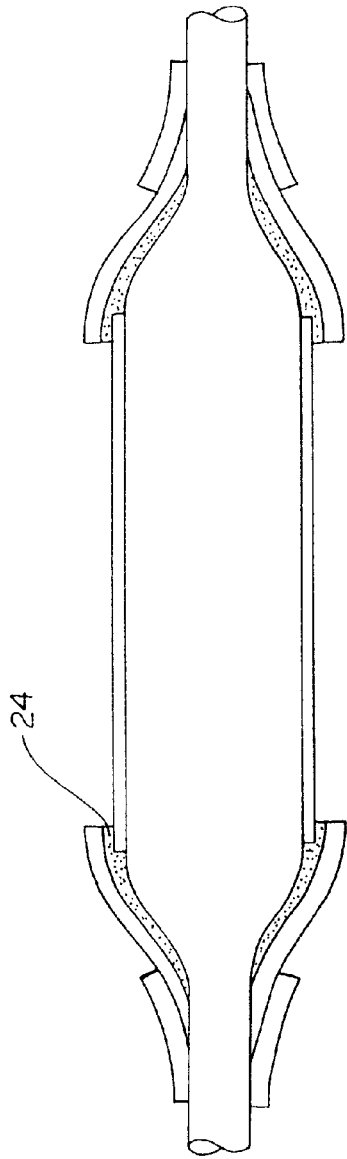
FIG. 5 is a side view of an embodiment of the invention.
Figure 6:
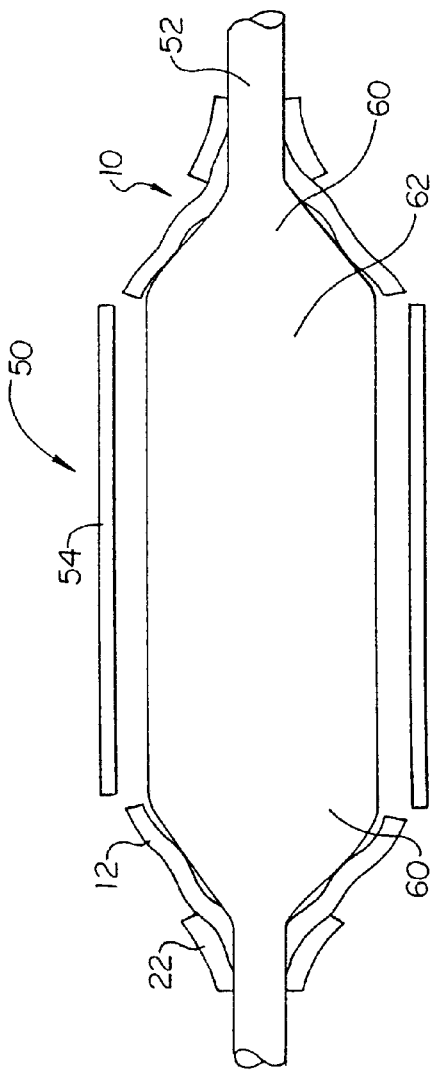
FIG. 6 is a side view of the embodiment shown in FIG. 3 in a potential post stent delivery state.

While, in FIG. 3 the inside surface 26 of section 32 of the second tubular member 22 is laser welded to the catheter shaft 52. A portion of the inside surface 14 of section 18 of the first tubular member 12 overlies each end of a stent 54 prior to stent delivery. As previously described, the inside surface 14 of the first tubular member may have a lubricant 24 applied thereto. The lubricant 24 may be applied to the entire inside surface 14 such as is seen in FIG. 5. Alternatively, the lubricant 24 may be selectively applied to only a portion of the sleeve, such as the portion of the sleeve 18 which overlies the stent 54, such as is shown in FIG. 4. As previously mentioned, the portion of the sleeve 18 which may overlay the stent 54, may be modified to have improved lubricity by treating at least a portion of the inside surface 14 prior to placement of the sleeves 10 on the stent delivery catheter 50. An example of such treatment would be to expose only portion 18 of the inside surface 14 to a plasma field as previously discussed.

Retraction of the sleeves 10 may occur in a variety of manners. For instance, in the embodiment shown in FIG. 6 the sleeves are constructed and arranged to retract off of only the ends of the stent 54, when the balloon 62 is inflated. In the embodiment shown in FIG. 6, the expansion of the balloon 62 combined with the elastic nature of the first tubular member 12 allows the sleeve to retract to an extent sufficient to allow the stent 54 to be released.

In an alternative embodiment shown in FIG. 7, the sleeves 10 are designed so that during stent delivery the sleeves will slide or roll off of the stent 54 as well as balloon cones 60. In the embodiment shown, the thickened portion 66 of the sleeve 10 (which results from the overlap of the first tubular member 12 and the second tubular member 22) acts as a breaking or folding point for the sleeve 10 whereupon portion 18 of the first tubular member 12 will tend to fold over and at least partially overlie during and subsequent to stent delivery. As may be seen, the thickened portion 66 may assist the retracted sleeve 10 into taking on an S-shaped retraction configuration. Such a configuration helps to ensure that the sleeve 10 is fully retracted off of the stent 54 and balloon 60.

An additional type of sleeve retraction is shown in FIG. 9 and is best accomplished by an alternative embodiment of the invention shown in FIG. 8, wherein a portion of the outside surface 28 of the second section 32 of the second tubular member 22 is engaged to the catheter shaft 52. In such an embodiment the second tubular member 22 is actually folded over on to itself where it is engaged to the catheter shaft 52. Such a folded over engagement may employ any of the engagement methods previously discussed. The folded over configuration shown in FIG. 8 provides the sleeve with a second breaking point 67 which provides a tension which assists in pulling the sleeve 19 completely off of stent 54 as well as the balloon cones 60 when the stent 54 is expanded.

In the various embodiments shown in FIGS. 3–9, the portion of the sleeve 26 which is in contact with the catheter shaft 52 may be at least partially affixed to the catheter shaft 52. In this embodiment one or both of the tubular members 12 and 22 may be configured to provide a "snapping" action so that the sleeve 10 is actively pulled off of the stent 54 in an elastic manner thereby providing an even greater tendency for the sleeves 10 to full retract off of the stent 54.

In addition to being directed to the embodiments described above and claimed below, the present invention is further directed to embodiments having different combinations of the features described above and claimed below. As such, the invention is also directed to other embodiments having any other possible, combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:

a catheter, the catheter having a stent mounting region and a catheter shaft;

a stent, the stent disposed about the stent mounting region, the stent characterized as having two ends; and at least one stent retaining sleeve, the at least one stent retaining sleeve having:

a fist tubular member, the first tubular member having a length, the first tubular member having a first portion and a second portion and an inside surface and an outside surface, at least a portion of the inside surface of the first portion of the first tubular member engagingly disposed about at least one end of the stent, the inside surface of the second portion of the first tubular member disposed about a portion of the catheter; and a second tubular member, the second tubular member having a length, the second tubular member having a first portion, a first portion end defined by the termination of the first portion, a second portion, a second portion end defined by the termination of the second portion, an inside surface and an outside surface, the inside surface of the first portion of the second tubular member overlapping the outside surface of at least the second portion of the first tubular member, the inside surface of the first portion of the second tubular member and the outside surface of the at least the second portion of the first tubular member being engaged to one another, wherein the first portion of the first tubular member extends from the first portion end of the second tubular member, the inside surface of the second portion of the second tubular member engagingly disposed about a portion of the catheter shaft, wherein less than half of the length of the first tubular member overlaps with the second tubular member.

2. A stent delivery system of 1, wherein the at least a portion of the inside surface of the first tubular member further comprises a lubricious surface.

3. The stent delivery system of claim 2, wherein the lubricious coating is at least partially composed of at least one member of the group consisting of one or more silicones, PVP, PPO, polyethylene oxide and neopentyl glycol diacrylate polymerized in a solution of water and isopropyl alcohol in the presence of a photoinitiator, oil, wax, and any combination thereof.

4. The stent delivery system of claim 2, the lubricious surface comprising a plasma enhanced surface, the plasma enhanced surface being produced by exposing the at least a portion of the inside surface of the first tubular member to a charged ion field, the charged ion field modifying the at least a portion of the inside surface of the first tubular member, thereby producing a modified surface having enhanced lubricity.

5. The stent delivery system of claim 4, wherein the modified surface is cross-linked.

6. The stent delivery system of claim 1, wherein the first tubular member is at least partially composed of an elastomeric polymer.

7. The stent delivery system of claim 1, wherein the first tubular member is at least partially composed of polyurethane.

8. The stent delivery system of claim 1, wherein the first tubular member is at least partially constructed from biocompatible medical grade aromatic polyurethane.

9. The stent delivery system of claim 1, wherein the second tubular member is composed at least partially of at least one member of the group consisting of: polyurethane, polycarbonate-polyurethane co-polymer, polyurethane-polycarbonate blends, and any combination thereof.

10. The stent delivery system of claim 1, wherein the second tubular member is composed of a combination of polyurethane and at least one polyurethane-polycarbonate blend.

11. The stent delivery system of claim 1, wherein the second tubular member is composed of a combination of first polycarbonate-polyurethane co-polymer and a second polycarbonate-polyurethane co-polymer.

12. The stent delivery system of claim 11, wherein the combination further comprises substantially 50 percent of the first polycarbonate-polyurethane co-polymer and substantially 50 percent of the second polycarbonate-polyurethane co-polymer.

13. The stent delivery system of claim 1, wherein at least a portion of the inside surface of the first portion of the second tubular member is fixedly engaged to at least a portion of the outside surface of at least the second portion of the first tubular member.

14. The stent delivery system of claim 13, wherein the at least a portion of the inside surface of the first portion of the second tubular member is heat welded to the at least a portion of the outside surface of at least the second portion of the first tubular member.

15. The stent delivery system of claim 13, wherein the at least a portion of the inside surface of the first portion of the second tubular member is laser welded to the at least a portion of the outside surface of at least the second portion of the first tubular member.

16. The stent delivery system of claim 13, wherein the at least a portion of the inside surface of the first portion of the second tubular member is chemically bonded to the at least a portion of the outside surface of at least the second portion of the first tubular member.

17. The stent delivery system of claim 13, wherein the at least a portion of the inside surface of the first portion of the second tubular member is physically bonded to the at least a portion of the outside surface of at least the second portion of the first tubular member.

18. The stent delivery system of claim 13, wherein the at least a portion of the inside surface of the first portion of the second tubular member overlaps in an interference fit the at least a portion of the outside surface of at least the second portion of the first tubular member.

19. The stent delivery system of claim 1, wherein at least a portion of the inside surface of the second portion of the second tubular member is frictionally engaged to at least a portion of the catheter shaft.

20. The stent delivery system of claim 1, wherein the inner surface of the second portion of the second tubular member is fixedly engaged to at least a portion of the catheter shaft.

21. The stent delivery system of claim 1, wherein the inner surface of the second portion of the second tubular member is heat welded to at least a portion of the catheter shaft.

22. The stent delivery system of claim 1 wherein the inner surface of the second portion of the second tubular member is laser welded to at least a portion of the catheter shaft.

23. The stent delivery system of claim 1, wherein the inner surface of the second portion of the second tubular member is chemically bonded to at least a portion of the catheter shaft.

24. The stent delivery of claim 1, wherein the inner surface of the second portion of the second tubular member is physically bonded to at least a portion of the catheter shaft.

25. The stent delivery system of claim 1, wherein the first tubular member is elastic.

26. The stent delivery system of claim 25, wherein the first tubular member is made from a material comprising polyurethane.

27. A stent delivery system comprising:
  a catheter, the catheter having a stent mounting region and a catheter shaft;
  a stent, the stent disposed about the stent mounting region, the stent characterized as having two ends;
  at least one stent retaining sleeve, the at least one stent retaining sleeve having:
    a first tubular member, the first tubular member having a length, a first portion and a second portion and an inside surface and an outside surface, at least a portion of the inside surface of the first tubular member having a lubricious coating thereon, the inside surface of the first portion of the first tubular member engagingly disposed about at least one end of the stent, the inside surface of the second portion of the first tubular member disposed about a portion of the catheter;
    a second tubular member, the second tubular member having a length, a first portion, a first portion end defined by the termination of the first portion and a second portion, a second portion end defined by the termination of the second portion, and an inside surface and an outside surface, the inside surface of the first portion of the second tubular member overlapping the outside surface of at least the second portion of the first tubular member, the inside surface of the first portion of the second tubular member and the outside surface of the at least the second portion of the first tubular member being engaged to one another, wherein the first portion of the first tubular member extends from the first portion end of the second tubular member and less than half of the length of the first tubular member overlaps with the second tubular member, the second portion at least partially folded over on to itself whereby the outer surface of the second portion of the second tubular member is engagingly disposed about at least a portion of the catheter shaft.

28. The stent retaining sleeve of claim 27, wherein the first tubular member is elastic.

29. The stent retaining sleeve of claim 28, wherein the first tubular member is made from a material comprising polyurethane.

* * * * *